US008460607B2

(12) United States Patent
Yang

(10) Patent No.: US 8,460,607 B2
(45) Date of Patent: Jun. 11, 2013

(54) MICROFLUIDIC DEVICE HAVING A FLOW CHANNEL

(75) Inventor: Tahua Yang, Woodridge, IL (US)

(73) Assignee: Abbott Laboratories, Abbott Park, IL (US)

( * ) Notice: Subject to any disclaimer, the term of this patent is extended or adjusted under 35 U.S.C. 154(b) by 93 days.

(21) Appl. No.: 12/910,031

(22) Filed: Oct. 22, 2010

(65) Prior Publication Data

US 2012/0100041 A1 Apr. 26, 2012

(51) Int. Cl.

*G01N 33/00* (2006.01)
*G01N 33/48* (2006.01)
*B01L 3/00* (2006.01)

(52) U.S. Cl.

USPC ....... 422/82.05; 422/68.1; 422/243; 422/417; 422/503; 435/288.7; 356/445

(58) Field of Classification Search

None

See application file for complete search history.

(56) References Cited

U.S. PATENT DOCUMENTS

| | | | | |
|---|---|---|---|---|
| 4,844,097 | A * | 7/1989 | Bellhouse et al. | 600/352 |
| 4,973,561 | A * | 11/1990 | Hansen et al. | 436/52 |
| 5,494,640 | A * | 2/1996 | Simon et al. | 422/82.05 |
| 5,885,470 | A | 3/1999 | Parce et al. | |
| 6,043,080 | A | 3/2000 | Lipshutz et al. | |
| 6,051,437 | A * | 4/2000 | Luo et al. | 436/172 |
| 6,326,211 | B1 | 12/2001 | Anderson et al. | |
| 6,409,832 | B2 | 6/2002 | Weigl et al. | |
| 6,415,821 | B2 | 7/2002 | Kamholz et al. | |
| 6,615,856 | B2 | 9/2003 | McNeely et al. | |
| 6,811,752 | B2 | 11/2004 | Barbera-Guillem | |
| 6,900,889 | B2 * | 5/2005 | Bjornson et al. | 356/246 |
| 7,244,393 | B2 * | 7/2007 | Kaylor et al. | 422/412 |
| 2001/0036672 | A1 | 11/2001 | Anderson et al. | |
| 2003/0113931 | A1 * | 6/2003 | Pan et al. | 436/113 |
| 2005/0148091 | A1 | 7/2005 | Kitaguchi et al. | |
| 2006/0263874 | A1 * | 11/2006 | Kunuki et al. | 435/287.2 |
| 2007/0172388 | A1 | 7/2007 | Padmanabhan et al. | |
| 2008/0260742 | A1 * | 10/2008 | Sato et al. | 424/139.1 |
| 2008/0290037 | A1 | 11/2008 | Liu | |
| 2009/0014360 | A1 | 1/2009 | Toner et al. | |
| 2009/0029870 | A1 | 1/2009 | Ward et al. | |

(Continued)

FOREIGN PATENT DOCUMENTS

| | | | |
|---|---|---|---|
| EP | 1671700 | A2 | 6/2006 |
| EP | 2062644 | A1 | 5/2009 |

(Continued)

OTHER PUBLICATIONS

M.T. Jeppesen and E.H. Hansen, Determination of creatine in undiluted blood serum by enzymatic flow injection analysis with optosensing, 1988, Analytica Chimica Acta, v. 214, pp. 147-159.*

(Continued)

*Primary Examiner* — Bobby Ramdhanie
*Assistant Examiner* — Timothy G Kingan
(74) *Attorney, Agent, or Firm* — Hanley, Flight & Zimmerman, LLC

(57) ABSTRACT

A microfluidic device having a flow channel comprising a hydrophobic membrane to improve control of flow and control of processing conditions in the flow channel, and to improve the removal of gas bubbles from the flow channel of the microfluidic device. In addition, the invention enables the process controls of the microfluidic device to know when gas bubbles have been removed, so that the next step in the process can be carried out.

31 Claims, 8 Drawing Sheets

U.S. PATENT DOCUMENTS

| | | | | |
|---|---|---|---|---|
| 2009/0047713 | A1* | 2/2009 | Handique | 435/91.2 |
| 2009/0048805 | A1 | 2/2009 | Kaduchak et al. | |
| 2009/0053106 | A1 | 2/2009 | Wu et al. | |
| 2009/0107909 | A1 | 4/2009 | Kotera et al. | |
| 2009/0147253 | A1 | 6/2009 | Hartmann et al. | |
| 2009/0158823 | A1 | 6/2009 | Kaduchak et al. | |
| 2009/0162887 | A1 | 6/2009 | Kaduchak et al. | |
| 2009/0188795 | A1 | 7/2009 | Oakey et al. | |

FOREIGN PATENT DOCUMENTS

| | | | |
|---|---|---|---|
| WO | WO2004061418 | A2 | 7/2004 |
| WO | 2007001912 | A1 | 1/2007 |
| WO | WO2007044548 | A2 | 4/2007 |
| WO | WO2007060523 | A1 | 5/2007 |
| WO | 2009086043 | A2 | 7/2009 |
| WO | 2009123555 | A1 | 10/2009 |

OTHER PUBLICATIONS

Abbott Laboratories, Abbott Park, IL, USA, AEROSET® Systems Operations Manual, 200154-101—Nov. 2004, pp. 3-7, 3-9, 3-10, 3-11.

Armani et al., Fabricating PDMS Microfluidic Channels Using a Vinyl Sign Plotter, *Lab on a Chip Technology, Volume 1: Fabrication and Microfluidics*, edited by Herold, K. E. and Rasooly, A., Caister Academic Press (Norfolk, UK: 2009), pp. 9-15.

Carlen et al., Silicon and Glass Micromachining, *Lab on a Chip Technology, Volume 1: Fabrication and Microfluidics*, edited by Herold, K. E. and Rasooly, A., Caister Academic Press (Norfolk, UK: 2009), pp. 83-114.

Cheung et al., Microfluidics-based Lithography for Fabrication of Multi-Component Biocompatible Microstructures, *Lab on a Chip Technology, Volume 1: Fabrication and Microfluidics*, edited by Herold, K. E. and Rasooly, A., Caister Academic Press (Norfolk, UK: 2009), pp. 115-124.

Lee, Microtechnology to Fabricate Lab-on-a-Chip for Biology Applications, *Lab on a Chip Technology, Volume 1: Fabrication and Microfluidics*, edited by Herold, K. E. and Rasooly, A., Caister Academic Press (Norfolk, UK: 2009), pp. 125-138.

Microfluidics—Wikipedia, the free encyclopedia, [online]. 2010 [retrieved on Sep. 13, 2010]. Retrieved from the Internet: <URL: http://en.wikipedia.org/wiki/Microfluidics>, pp. 1-7.

Nguyen, Nam-Trung et al., *Fundamentals and Applications of Microfluidics*, Second Edition, Artech House (Norwood, MA, USA: 2006), pp. 55-115.

OEM GE Nylon—Hydrophobic Membranes. Datasheet [online]. General Electric Company, 2010 [retrieved on Oct. 20, 2010]. Retrieved from the Internet: <URL: http://www.osmolabstore.com/OsmoLabPage.dll?BuildPage&1&1&1021>, pp. 1-2.

Package Insert, Architect/Aeroset Creatinine, Ref 7D64-20, Abbott Laboratories, Abbott Park, IL, USA, Nov. 2006, pp. 1-8.

Package Insert, Architect/Aeroset Multiagent Ethanol; Ref 3L36-20, Abbott Laboratories, Abbott Park, IL, USA, Jul. 2009, pp. 1-6.

Package insert, Architect/Aeroset Multigent Cocaine, Ref 3L40-20, Abbott Laboratories, Abbott Park, IL, USA, Jul. 2009, pp. 1-8.

Spectrophotometry—Wikipedia, the free encyclopedia, [online]. 2010 [retrieved on Oct. 21, 2010]. Retrieved from the Internet: <URL: http://en.wikipedia.org/wiki/Spectrophotometer>, pp. 1-4.

Sun et al., Laminated Object Manufacturing (LOM) Technology-Based Multi-Channel Lab-on-a-Chip for Enzymatic and Chemical Analysis, *Lab on a Chip Technology, Volume 1: Fabrication and Microfluidics*, edited by Herold, K. E. and Rasooly, A., Caister Academic Press (Norfolk, UK: 2009), pp. 161-172.

Tabeling, *Introduction to Microfluidics*, Oxford University Press (New York: 2005), pp. 244-281.

Tsao et al., Bonding Techniques for Thermoplastic Microfluidics, *Lab on a Chip Technology, Volume 1: Fabrication and Microfluidics*, edited by Herold, K. E. and Rasooly, A., Caister Academic Press (Norfolk, UK: 2009), pp. 45-63.

Ultrasonic welding—Wikipedia, the free encyclopedia, [online]. 2010 [retrieved on Oct. 21, 2010]. Retrieved from the Internet: <URL: http://en.wikipedia.org/wiki/Ultrasonic_welding>, pp. 1-6.

Waddell, Laser Micromachining, *Lab on a Chip Technology, Volume 1: Fabrication and Microfluidics*, edited by Herold, K. E. and Rasooly, A., Caister Academic Press (Norfolk, UK: 2009), pp. 173-184.

Kersaudy-Kerhoas M., et al., "Hydrodynamic Blood Plasma Separation in Microfluidic Channels," Microfluidics and Nanofluidics, 2009, vol. 8 (1), pp. 105-114.

Data Sheet IMGVRMENb, Versapor R Membrane, Pall Corporation, 2011.

International Search Report and Written Opinion for Application No. PCT/US2011/057201, mailed on Feb. 23, 2012, 12 pages.

* cited by examiner

MICROFLUIDIC DEVICE HAVING A FLOW CHANNEL

BACKGROUND OF THE INVENTION

1. Field of the Invention

This invention relates to a system for removing gas bubbles from a flow channel in a microfluidic device.

2. Discussion of the Art

Microfluidic devices are designed to carry out analytical processes in a limited space, i.e., small reaction chambers and flow channels. In a sealed microfluidic device, the formation of gas bubbles in the flow channels is inevitable on account of such operational steps as mixing, dilution, separation, and other steps. In general, gas bubbles are removed from solutions by incorporating vent holes in a conduit to allow gas to escape. Gas bubbles in microfluidic devices occur when the flow channels of the devices are not fully primed. Gas bubbles are formed when plugs of liquid collide during a mixing step. Gas bubbles are formed by electrolysis of water around electrodes when the flow of liquid is driven by electrokinetic forces. The presence of gas bubbles adversely affects the precision of the rate of flow. The presence of gas bubbles also adversely affects the mixing of liquids. Gas bubbles act as an insulating layer for electrokinetic pumping.

Gas bubbles often interfere with optical measurements, if optical detection is required. Optical signals cannot differentiate a gas from a liquid. The presence of gas bubbles in flow channels makes it difficult to determine accurate quantities of reagents for chemical reactions. If chemical reactions are called for, reaction kinetics cannot be controlled on account of the uncertainty of the volume of gas and interference caused by the presence of gas bubbles. For liquids having a high surface tension, such as, for example, water, gas bubbles present an obstacle to flow in a flow channel. Liquids containing gas bubbles are less likely to wet the walls of the flow channel and flow in the microfluidic device.

For the foregoing reasons, trapped or dissolved gases should be removed from flow channels for microfluidic analysis.

U.S. Pat. No. 6,326,211 discloses a miniaturized integrated nucleic acid diagnostic device and system. The device is capable of performing one or more sample acquisition and preparation operations, in combination with one or more sample analysis operations. For example, the device can integrate several or all of the operations involved in sample acquisition and storage, sample preparation and sample analysis, within a single integrated unit. The device can be used in nucleic acid based diagnostic applications and de novo sequencing operations. However, the device and system described herein cannot control the timing of an actual chemical reaction subsequent to the mixing step. The patent is concerned only with mixing and does not consider reactions of chemicals and detection of the reaction product.

U.S. Pat. No. 6,811,752 discloses a device comprising a plurality of microchambers having a closed vented environment, wherein each microchamber is in operative communication with a filling port and a vent aperture. The device further comprises a base which is sandwiched between two liquid-impermeable membranes, with at leas one of the membranes being gas permeable. This reference also discloses a method for introducing a fluid into a plurality of microchambers of the device, wherein each filling port is aligned with a pipette tip, and the fluid is introduced into and through the filling port. The fluid then flows along a fluid flow groove providing fluid flow communication between the filling port and the microchamber, and into the microchamber. However, the device requires external pumps and valves. The patent does not disclose microchannels and removal of localized gas bubbles, nor does the patent disclose detection of gas bubbles to control reaction kinetics.

U.S. Pat. No. 6,615,856 discloses a method of controlling fluid flow within a microfluidic circuit using external valves and pumps connected to the circuit. The external valves and pumps, which are not part of the microfluidic substrate, control fluid pumping pressure and the displacement of air out of the fluid circuit as fluid enters into the circuit. If a valve is closed, air cannot be displaced out of circuit, which creates a pneumatic barrier that prevents fluid from advancing within the circuit (under normal operating pressures). However, the device requires external pumps and valves.

U.S. Pat. No. 6,409,832 discloses a device for promoting protein crystal growth (PCG) using flow channels of a microfluidic device. A protein sample and a solvent solution are combined within a flow channel of a microfluidic device having laminar flow characteristics which forms diffusion zones, providing for a well defined crystallization. Protein crystals can then be harvested from the device. However, the device requires external pumps and valves.

U.S. Pat. No. 6,415,821 discloses magnetically actuated fluid handling devices using magnetic fluid to move one or more fluids through microsized flow channels. Fluid handling devices include micropumps and microvalves. Magnetically actuated slugs of magnetic fluid are moved within microchannels of a microfluidic device to facilitate valving and/or pumping of fluids and no separate pump is required. The magnets used to control fluid movement can be either individual magnets moved along the flow channels or one or more arrays of magnets whose elements can be individually controlled to hold or move a magnetic slug. Fluid handling devices include those having an array of electromagnets positioned along a flow channel which are turned on and off in a predetermined pattern to move magnetic fluid slugs in desired paths in the flow channel. However, the device requires external pumps and valves. The patent does not mention hydrophobic membranes, nor does it mention removal of gas bubbles. The patent also does not disclose reaction kinetics.

WO 2007001912 discloses a reservoir for use in testing a liquid as part of a microfluidic testing system. The microfluidic testing system includes a testing chamber configured to receive the liquid to be tested. A liquid inlet is fluidly coupled to the testing chamber to allow ingress of the liquid into the testing chamber. A gas outlet is fluidly coupled to the testing chamber to allow egress of gas out of the testing chamber. The gas outlet has an elevation that is higher than the elevation of the liquid inlet such that, as the testing chamber is rotated, the gas is expelled out of the testing chamber through the gas outlet, thereby reducing or preventing a presence of gas bubbles in the liquid. This device does not make use of a hydrophobic membrane to aid in the removal of gas bubbles.

EP 1671700 discloses a method of controlling environmental conditions within a fluidic system, e.g., preventing bubble formation, where such environmental conditions can affect the operation of the system in its desired function. Such environmental conditions are generally directed to the fluids themselves, the movement of such fluids through these systems, and the interaction of these fluids with other components of the system, e.g., other fluids or solid components of the system. This system does not use a vent or a hydrophobic membrane to remove gas bubbles during the process.

Microfluidic devices exhibit numerous advantages as compared with devices having conventional flow channels. Microfluidic devices dramatically reduce the quantities of reagents and samples, thereby resulting in lowered costs.

Microfluidic devices reduce the quantities of hazardous materials, e.g., biohazardous materials and organic solvents. Microfluidic devices require a smaller amount of floor space than do conventional analyzers. Microfluidic devices enable integration of various unit operations, such as, for example, separation, mixing, reacting, and detecting. Microfluidic devices enable assays to be carried out in a lesser amount of time, as compared with the time required by conventional diagnostic analyzers. Microfluidic devices can be automated with little difficulty, thereby enhancing consistency and reproducibility of test results.

Detection of gas bubbles is required because access to and control of the chemical reaction or kinetics as reactants pass through the system is difficult. Detection of gas bubbles enables controlling the commencement of mixing, reacting, and detecting in assays where determination of the concentration of an analyte is based on the measurements related to certain rates, such as, for example, rates of change in a given parameter. An example of such a parameter is absorbance. See, for example, FIG. 3.1 in AEROSET® Systems Operations Manual, 200154-101-November 2004, page 3-7, incorporated herein by reference.

SUMMARY OF THE INVENTION

This invention provides a microfluidic device having a flow channel comprising a hydrophobic membrane to improve control of flow and control of processing conditions in the flow channel, and to improve the removal of gas bubbles from the flow channel of the microfluidic device. In addition, the invention enables the process controls of the microfluidic device to know when gas bubbles have been removed, so that the next step in the process can be carried out.

The hydrophobic membrane is capable of allowing gases to escape from the flow channel, while continuing to enable retention of liquid in the flow channel. The material for constructing the hydrophobic membrane should be chemically compatible with the material of the flow channel of the microfluidic device to facilitate assembly. Processes that can be used to fabricate the microfluidic device include, but are not limited to, ultrasonic welding, heat sealing, solvent bonding, and adhesive bonding. Assembly is typically carried out by ultrasonic welding or heat sealing.

Control loops, which can be open loops or closed loops, are provided to synchronize and program reactions in the assay and other analytical activities in the microfluidic device. Sensors for monitoring and controlling assay steps and other analytical activities can be located at points in the flow channel where reagents are introduced, at points in the flow channel where reactants are mixed, at points in the flow channel where reactions take place, and at points in the flow channel where the results of reactions are read. A feedback loop can be provided to monitor the step of removing gas bubbles. It is preferred that monitoring be carried out by optical methods, such as, for example, reflection of light from the surface of the hydrophobic membrane. The information allows the microfluidic device to determine the beginning and the end of the step of removing gas bubbles from the flow channel.

The benefits and advantages of the microfluidic device described herein include, but are not limited to: (a) more accurate and consistent analytical results by removing the variations caused by gas bubbles; (b) accurate status of priming activities, if the flow channels need to be primed before reagents are introduced into the flow channels; (c) built-in quality checks of the flow channels by monitoring abnormal flow behavior of samples and reagents by means of optical monitoring; (d) ease of assembly of microfluidic devices by using thermoplastic materials for all required components of the device; (e) avoidance of degassing for those reagents that have a tendency to expel gas over a period of time; and (f) enable detection of reactions that generate gaseous byproducts.

BRIEF DESCRIPTION OF THE DRAWINGS

In FIG. 2D, there is no gas bubble in the flow channel.

In FIG. 2E, there is a gas bubble in the flow channel in register with the hydrophobic membrane.

In FIG. 5A, a gas bubble is present at the junction position.

In FIG. 5B, the gas bubble has been removed.

DETAILED DESCRIPTION

Figure 1A:
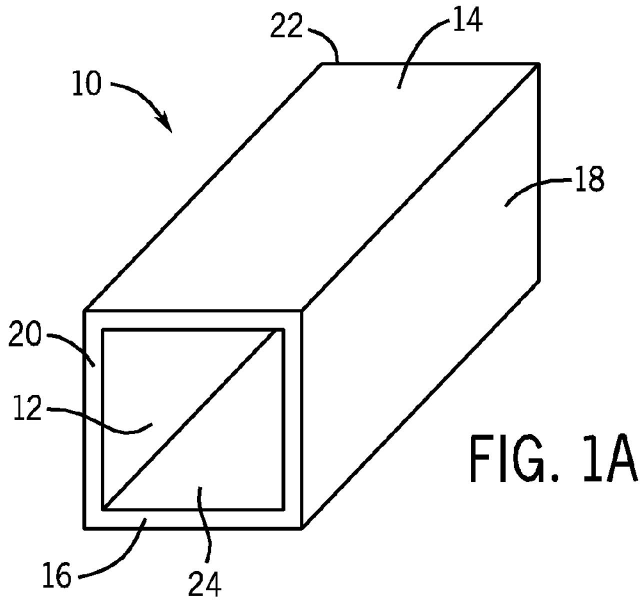
FIG. 1A is a perspective view of a flow channel of a microfluidic device.
Figure 1B:
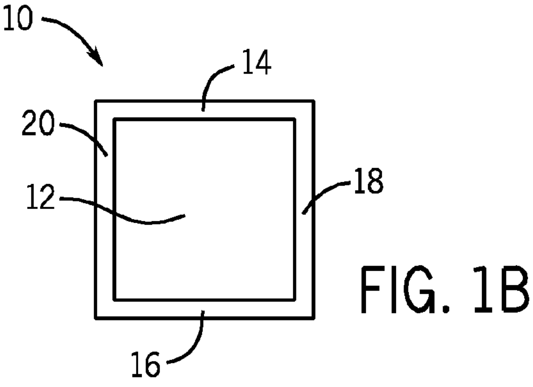
FIG. 1B is an end view of the flow channel shown in FIG. 1A.
Figure 1C:
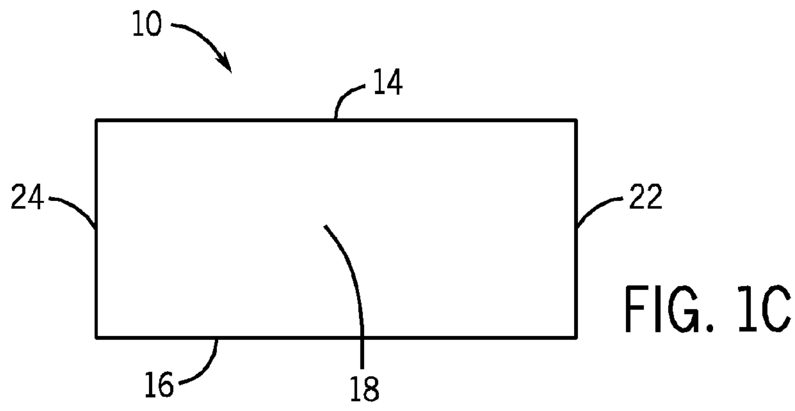
FIG. 1C is a side view of a wall of the flow channel shown in FIG. 1A.

As used herein, the expression "flow channel" means a tubular passage for liquids. As used herein, the expression "microfluidic device" means a physical element that enables the control and manipulation of fluids that are geometrically constrained to a small, typically sub-millimeter scale. Further discussion of microfluidics can be found at Microfluidics—Wikipedia, the free encyclopedia, [online]. 2010 [retrieved on Sep. 13, 2010]. Retrieved from the Internet: <URL: http://en.wikipedia.org/wiki/Microfluidics>, pages 1-7, incorporated herein by reference. Representative examples of materials that can be used to make microfluidic devices include, but are not limited to, silicone rubber, glass, plastic, silicon.

As used herein, the expression "hydrophobic membrane" means a thin sheet of natural or synthetic material that resists water while simultaneously venting gases. The hydrophobic material is preferably impermeable to water and other liquids while being permeable to gases.

As used herein, the terms "vent", "venting", and the like refer to discharge through a vent, i.e., an opening for the passage or escape of a gas or vapor.

As used herein, the term "feedback" means return of a portion of the output of a process or a system to input, especially to maintain performance or to control a system or a process. As used herein, the expression "feedback loop" means a system that relies on feedback for its operation.

As used herein, the expression "gas bubble" means a small globule of gas trapped in a liquid or solid.

A microfluidic device 10 suitable for use herein comprises a flow channel 12 comprising a top wall 14, a bottom wall 16, a first side wall 18, a second side wall 20. The flow channel 12 has an inlet 22 at the distal end thereof and an outlet 24 at the proximal end thereof. The dimensions of the flow channel 12 typically range from about 100 micrometers to about 1 millimeter in width and from about 100 micrometers to about 1 millimeter in height. The shape of the cross-section of the flow channel 12 need not be rectangular. The shape of the cross section of the flow channel 12 can be a polygon of any number of sides, e.g., three, four, five, six, seven, eight, etc. sides. Alternatively, the shape of the cross section of the flow channel can be curved, such as, for example, a continuous curve, e.g., circular, elliptical. The flow channel 12 can comprise a single conduit; alternatively, the flow channel can comprise two or more branches emerging from a single conduit or two or more branches joining to form a single conduit.

Figure 2A:
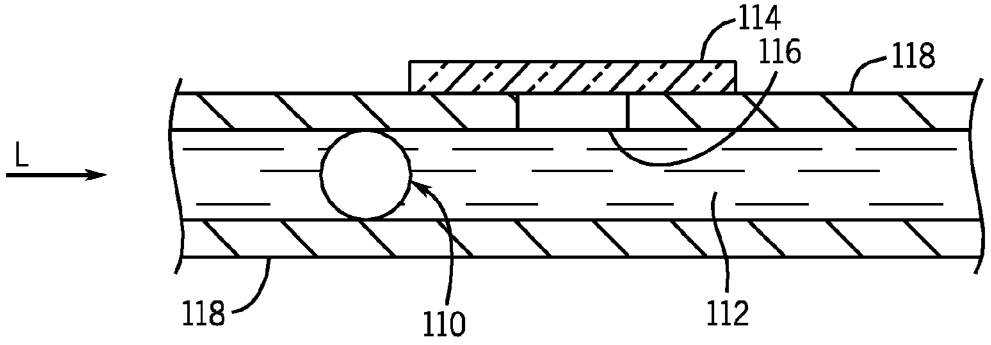
FIG. 2A is a schematic diagram, greatly enlarged, of a side view in elevation of a gas bubble in a flow channel of a microfluidic device, wherein the gas bubble is upstream of a hydrophobic membrane covering an aperture in the flow channel.
Figure 2B:
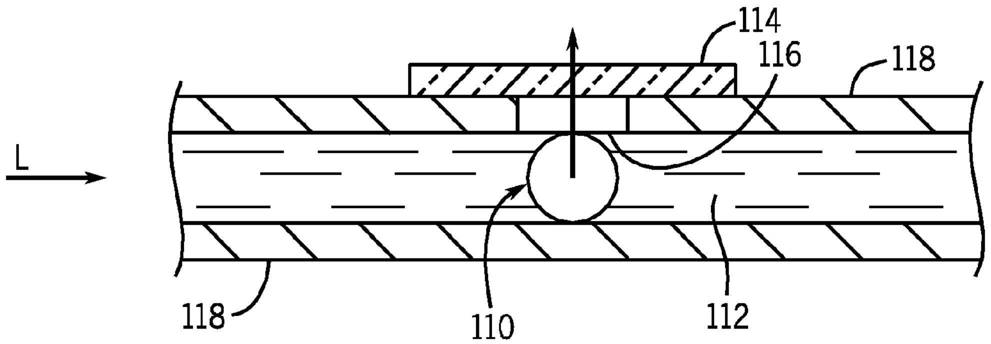
FIG. 2B is a schematic diagram, greatly enlarged, of a side view in elevation of a gas bubble in the flow channel of the microfluidic device of FIG. 2A, wherein the gas bubble is in register with the hydrophobic membrane covering the aperture in the flow channel.
Figure 2C:
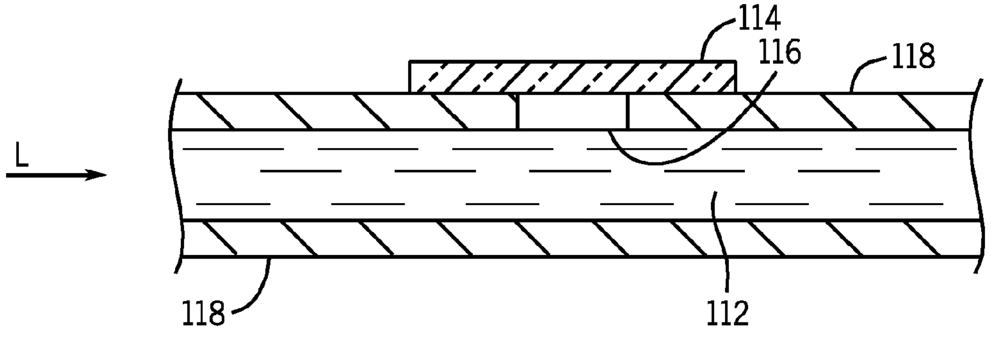
FIG. 2C is a schematic diagram, greatly enlarged, of a side view in elevation of the flow channel of the microfluidic device of FIG. 2A, wherein the gas bubble has been removed via the aperture in the flow channel, the aperture being covered by the hydrophobic membrane.

In the following figures, the arrow designated by the letter "L" indicates the direction of the flow of a liquid in the flow channel of a microfluidic device. FIG. 2A shows a gas bubble 110 in a flow channel 112 of a microfluidic device (not shown), wherein the gas bubble is upstream of a hydrophobic membrane 114. The hydrophobic membrane 114 covers an aperture 116 formed in a wall 118 constituting a boundary of the flow channel 112. The aperture typically has a major dimension, e.g., a diameter, ranging from about 2 millimeters to about 5 millimeters. FIG. 2B shows a gas bubble 110 in a flow channel 112 of a microfluidic device (not shown), wherein the gas bubble is in register with the hydrophobic membrane 114. The hydrophobic membrane 114 covers an aperture 116 formed in a wall 118 constituting a boundary of the flow channel 112. FIG. 2C shows a flow channel 112 of a microfluidic device (not shown), wherein the gas bubble has been removed through the hydrophobic membrane 114. The hydrophobic membrane 114 covers an aperture 116 formed in a wall 118 constituting a boundary of the flow channel 112.

Figure 2D:
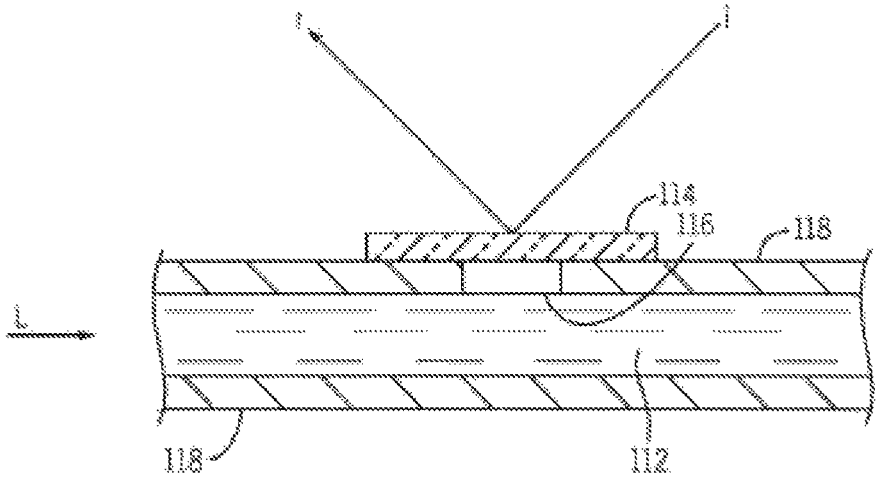
FIG. 2D is a schematic diagram, greatly enlarged, of a side view in elevation of a flow channel of a microfluidic device, wherein incident light is reflected from a surface of a hydrophobic membrane covering an aperture in the flow channel.

FIG. 2D shows a flow channel 112 of a microfluidic device (not shown). A hydrophobic membrane 114 covers an aperture 116 formed in a wall 118 constituting a boundary of the flow channel 112. There is no gas bubble in the flow channel. Incident light is reflected from the surface of the hydrophobic membrane 114 that is not facing the wall 118 constituting the boundary of the flow channel 112. The beam of incident light is represented by the symbol "i", and the reflected light is represented by the symbol "r." The incident light can be provided by a source of light, such as, for example, a lamp, that provides light at an appropriate wavelength. The reflected light can be detected by an appropriate light detector. A fiber optic sensor in contact with the surface of the hydrophobic membrane 114 that is not facing the wall 118 constituting the boundary of the flow channel 112 can be used to transmit incident light "i" to the flow channel 112 and to transmit reflected light "r" from the flow channel 112.

Figure 2E:
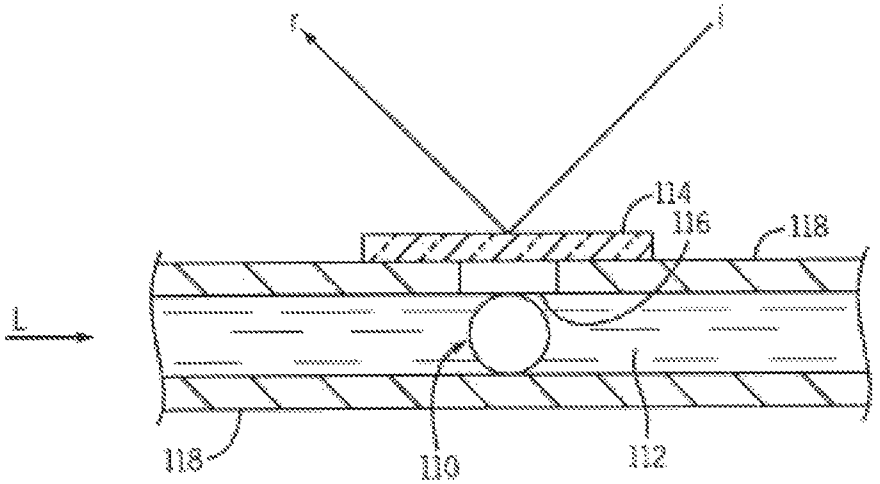
FIG. 2E is a schematic diagram, greatly enlarged, of a side view in elevation of the flow channel of the microfluidic device of FIG. 2D, wherein incident light is reflected from a surface of the hydrophobic membrane covering the aperture in the flow channel.

FIG. 2E shows a flow channel 112 of a microfluidic device (not shown) of FIG. 2D. A hydrophobic membrane 114 covers an aperture 116 formed in a wall 118 constituting a boundary of the flow channel 112. A gas bubble 110 is present in the flow channel. Incident light is reflected from a surface of the hydrophobic membrane 114 that is not facing the wall 118 constituting the boundary of the flow channel 112. When a gas bubble 110 is present in the flow channel, the quantity of light reflected by the surface of the hydrophobic membrane 114 is different from the quantity of light reflected by the surface of the hydrophobic membrane 114 when there is no gas bubble present in the flow channel. For additional information relating to detection of gas bubbles in flow channels of microfluidic devices, see, for example, Spectrophotometry—Wikipedia, the free encyclopedia, [online]. 2010 [retrieved on Oct. 10, 2010]. Retrieved from the Internet: <URL: http://en.wikipedia.org/wiki/Spectrophotometer>, incorporated herein by reference.

Figure 3:
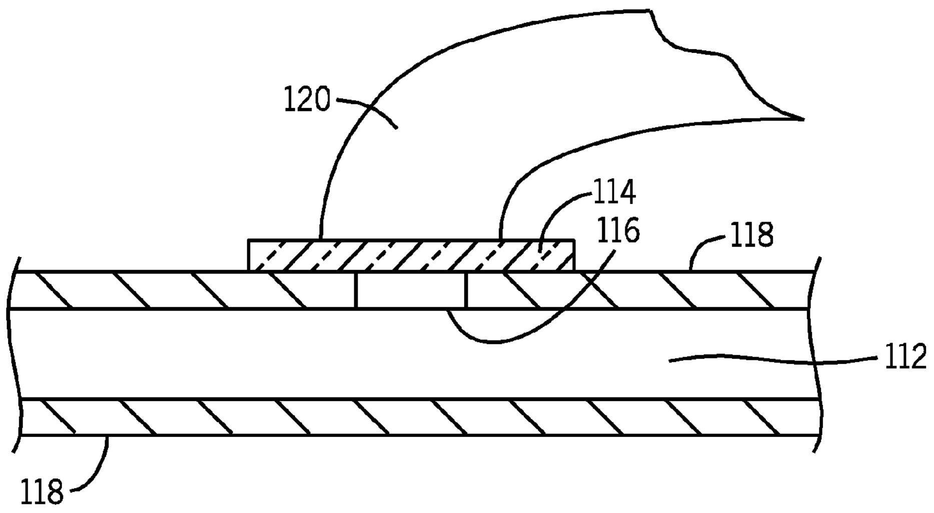
FIG. 3 is a schematic diagram, greatly enlarged, of a cross section of a flow channel of a microfluidic device, wherein a fiber optic sensor is in contact with a surface of a hydrophobic membrane covering an aperture in the flow channel.

FIG. 3 illustrates a flow channel 112 in a microfluidic device (not shown). A hydrophobic membrane 114 covers an aperture 116 formed in a wall 118 constituting a boundary of the flow channel 112. A fiber optic sensor 120 is in contact with the surface of the hydrophobic membrane 114 that is not facing the wall 118 constituting the boundary of the flow channel 112. A Thermo Fisher Scientific near-infrared analytical system having a fiber optic sensor can be employed for optical detection of gas bubbles.

Figure 4A:
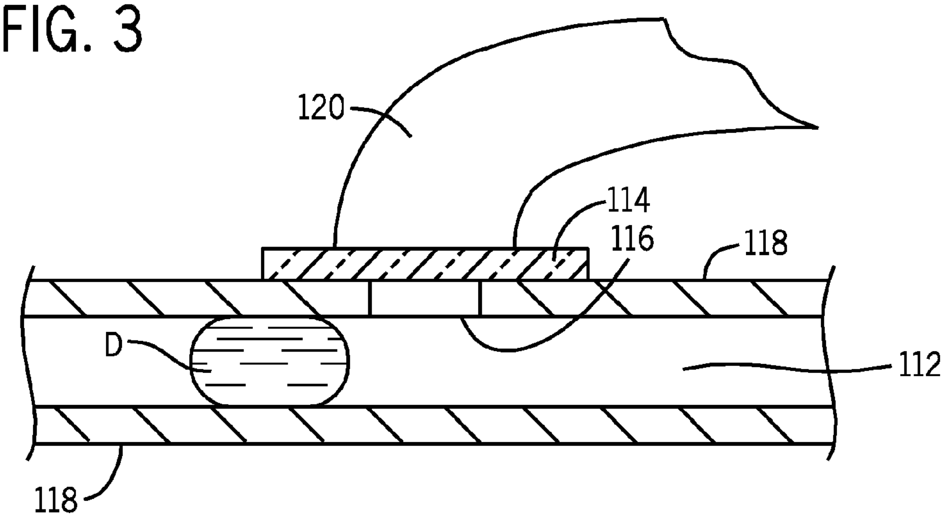
FIG. 4A is a schematic diagram, greatly enlarged, of a cross section of a flow channel of a microfluidic device, wherein a drop of liquid is upstream of a hydrophobic membrane covering an aperture in the flow channel. An optical monitoring sensor is in contact with a surface of the hydrophobic member. The microfluidic device is equipped to record the times at which two liquids combine and the times of subsequent operations in different locations of the flow channel.
Figure 4B:
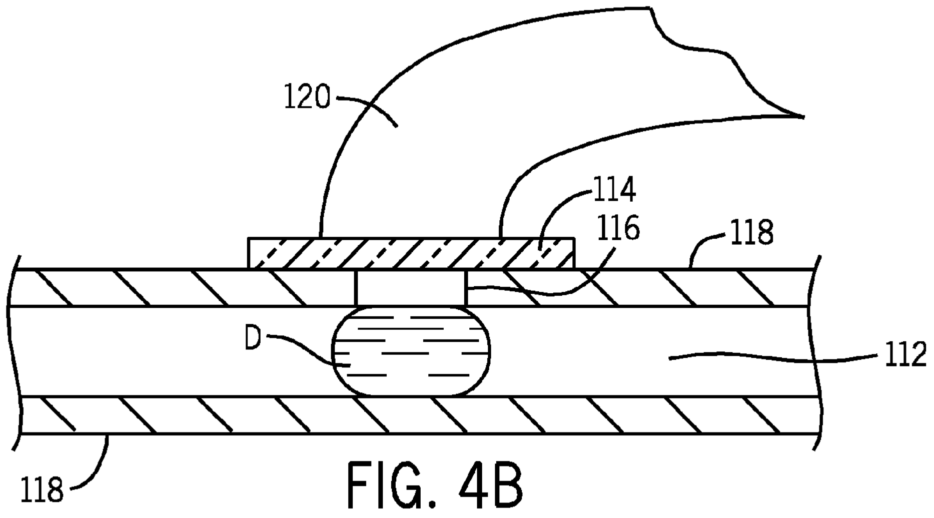
FIG. 4B is a schematic diagram, greatly enlarged, of the cross section of the flow channel of the microfluidic device of FIG. 4A, wherein the drop of liquid is in register with the hydrophobic membrane covering the aperture in the flow channel.
Figure 4C:
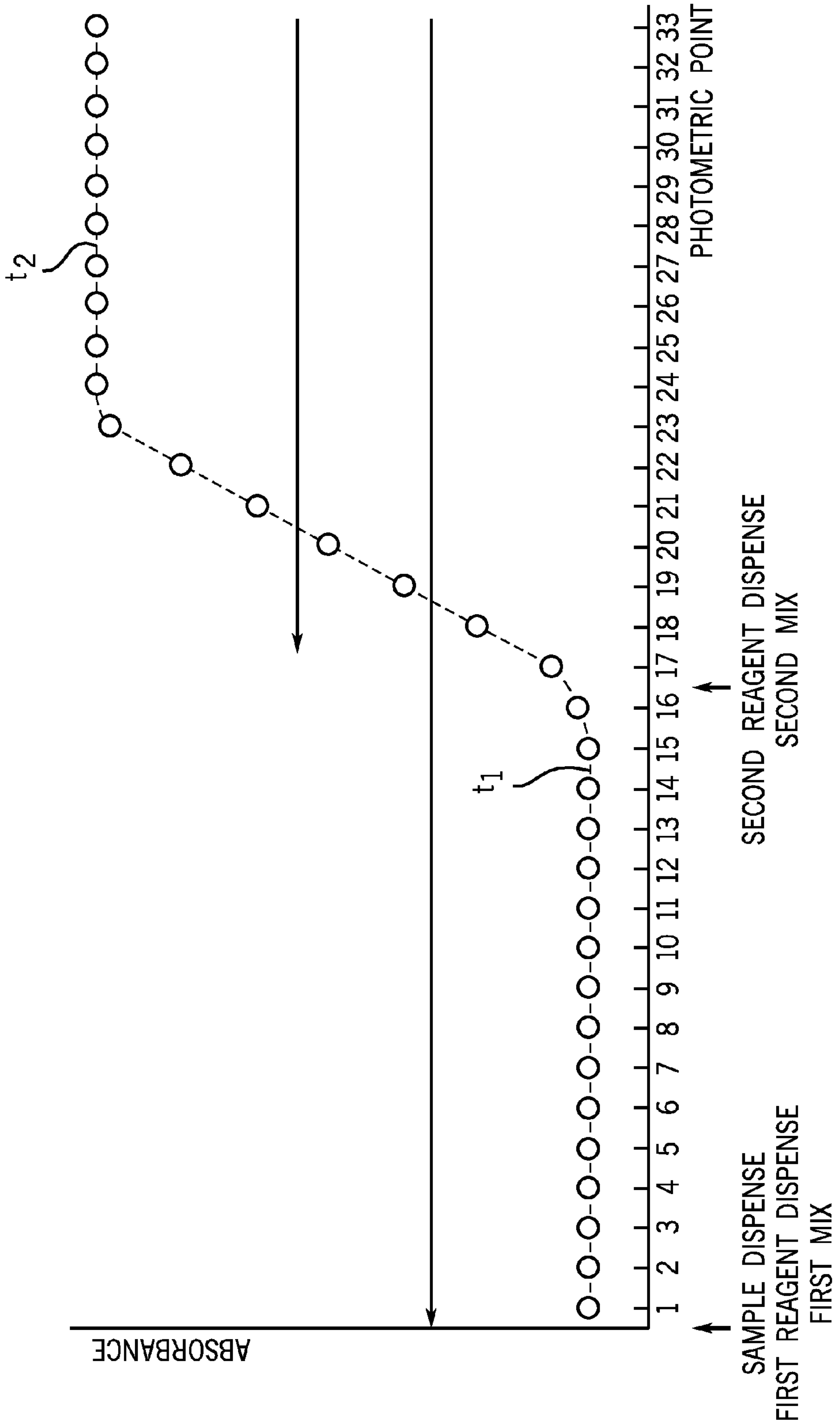
FIG. 4C is a graph illustrating absorbance as a function of time for the drop of liquid shown in FIGS. 4A and 4B.

FIG. 4A illustrates a flow channel 112 of a microfluidic device (not shown), wherein a drop of liquid "D" is upstream of a hydrophobic membrane 114. The hydrophobic membrane 114 covers an aperture 116 formed in a wall 118 constituting a boundary of the flow channel 112. A fiber optic sensor 120 is in contact with the surface of a hydrophobic membrane 114 that is not facing the wall 118 constituting the boundary of the flow channel 112. FIG. 4B illustrates a flow channel 112 of a microfluidic device (not shown), wherein a drop of liquid "D" is in register with a hydrophobic membrane 114. The hydrophobic membrane 114 covers an aperture 116 formed in a wall 118 constituting a boundary of the flow channel 112. The fiber optic sensor 120 is in contact with the surface of a hydrophobic membrane 114 that is not facing the wall 118 constituting the boundary of the flow channel 112. The fiber optic sensor 120 in contact with the surface of the hydrophobic membrane 114 that is not facing the wall 118 constituting the boundary of the flow channel 112 can be used to transmit incident light "i" to the flow channel 112 and to transmit reflected light "r" from the flow channel 112. The incident light can be provided by a source of light, such as, for example, a lamp, that provides light at an appropriate wavelength. The reflected light can be detected by an appropriate light detector. FIG. 4C is a graph illustrating absorbance as a function of time for the drop of liquid "D" shown in FIG. 4A and FIG. 4B. FIG. 4A represents the microfluidic device at time "$t_1$". FIG. 4B represents the microfluidic device at time "$t_2$". FIG. 4C graphically depicts the absorbance measured for the microfluidic device at time "$t_1$". FIG. 4C also graphically depicts the absorbance measured for the microfluidic device at time "$t_2$".

Figure 5A:
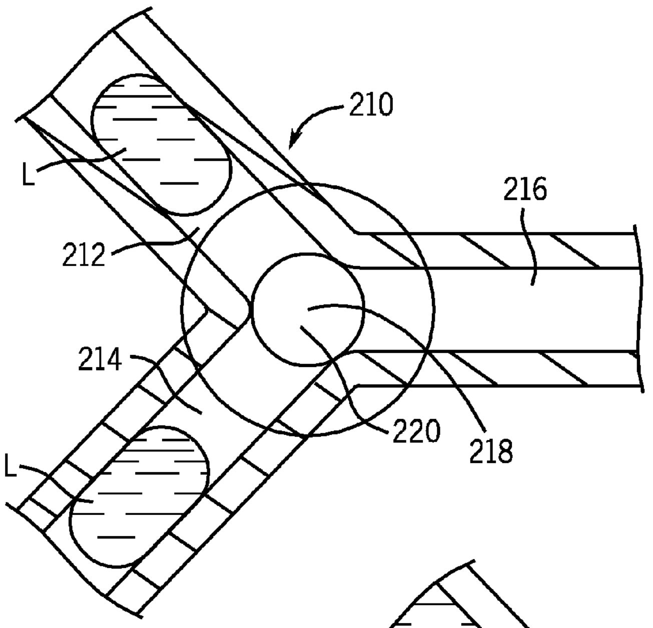
FIG. 5A is a schematic diagram, greatly enlarged, of a top view of a flow channel of a microfluidic device comprising of two branches joining at a junction position to form a single conduit.
Figure 5B:
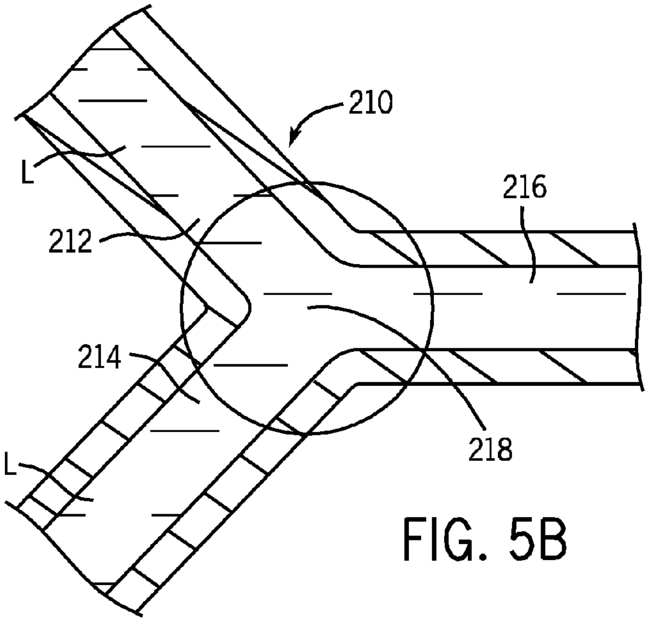
FIG. 5B is a schematic diagram, greatly enlarged, of a top view of the flow channel of the microfluidic device of FIG. 5A.

FIG. 5A illustrates a flow channel 210 of a microfluidic device (not shown). The flow channel 210 comprises a first branch 212, a second branch 214, and a single conduit 216, all of which converge at a junction 218. In this figure, a gas bubble 220 is present at the junction 218. FIG. 5B illustrates the flow channel 210 of a microfluidic device (not shown) of FIG. 5A. In this figure, the gas bubble has been removed. Liquid is represented by the letter "L".

Figure 6:
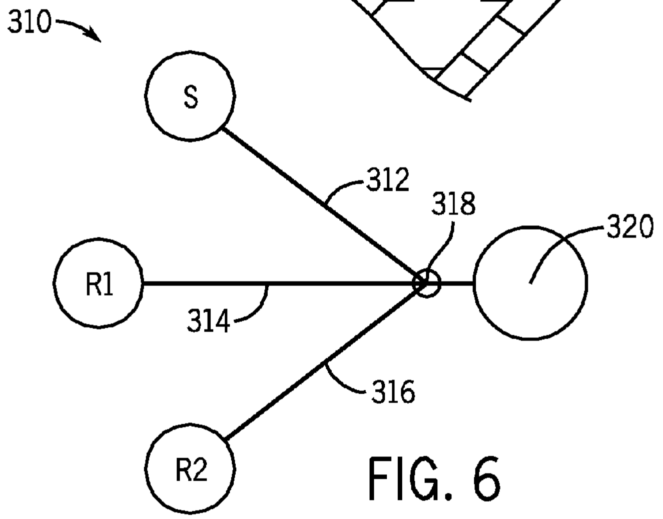
FIG. 6 is a schematic diagram illustrating a flow channel in a microfluidic device. In this scheme, liquids introduced at three separate locations of the microfluidic device can be combined. The microfluidic device of FIG. 6 comprises a single vent.

FIG. 6 illustrates a flow channel 310 of a microfluidic device (not shown), wherein liquids introduced in three separate branches of the flow channel 310 can be combined. In the first branch 312, a sample, designated by the letter "S", is introduced. In the second branch 314, a first reagent, designated by the alphanumeric characters "R1", is introduced. In the third branch 316, a second reagent, designated by the alphanumeric characters "R2", is introduced. The flow channel 310 comprises a single vent 318. The detection area 320 includes a spectrophotometer. The vent 318 is covered by a hydrophobic membrane (not shown). The vent 318 is an aperture of the type described previously.

Figure 7:
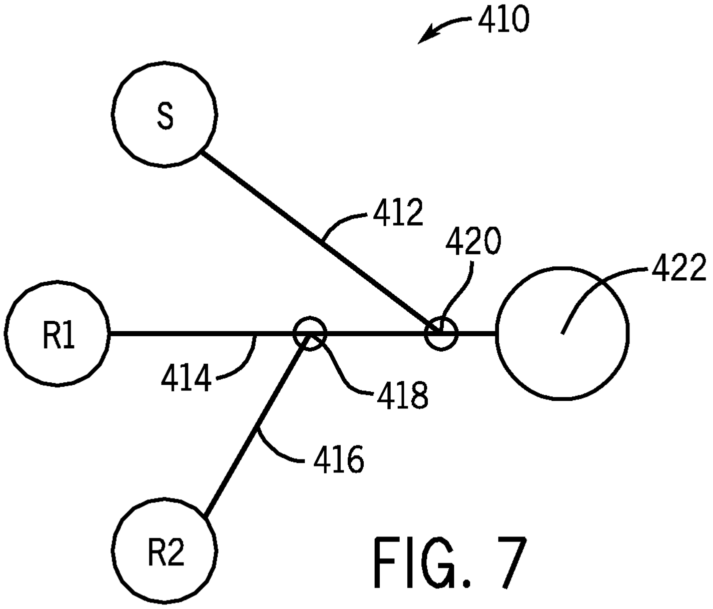
FIG. 7 is a schematic diagram illustrating a flow channel in a microfluidic device. In this scheme, liquids introduced at three separate locations of the microfluidic device can be combined. The microfluidic device of FIG. 7 comprises two vents.

FIG. 7 illustrates a flow channel 410 of a microfluidic device (not shown), wherein liquids introduced in three separate branches of the flow channel 410 can be combined. In the first branch 412, a sample, designated by the letter "S", is introduced. In the second branch 414, a first reagent, designated by the alphanumeric characters "R1", is introduced. In the third branch 416, a second reagent, designated by the alphanumeric characters "R2", is introduced. The flow channel 410 comprises two vents 418 and 420. The detection area 422 includes a spectrophotometer. Each vent 418 and 420 is covered by a hydrophobic membrane (not shown). The vents 418 and 420 are apertures of the type described previously.

Figure 8:
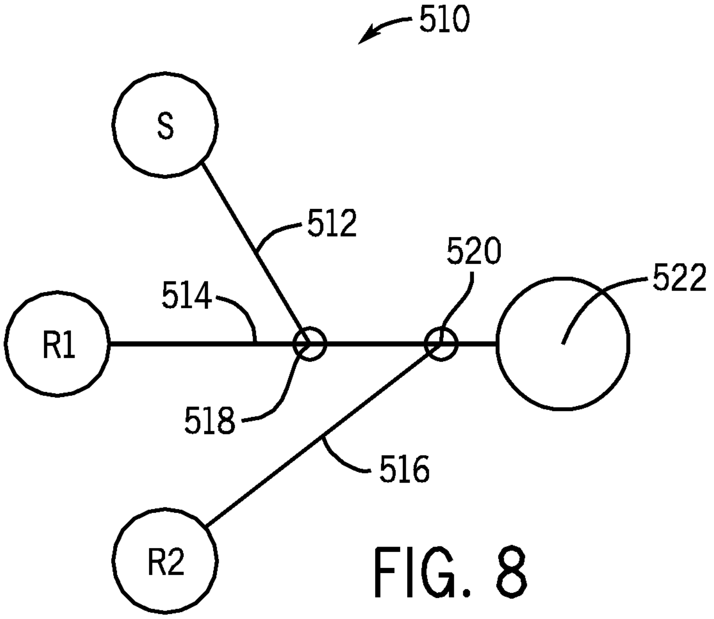
FIG. 8 is a schematic diagram illustrating a flow channel in a microfluidic device. In this scheme, liquids introduced at three separate locations of the microfluidic device can be combined. The microfluidic device of FIG. 8 comprises two vents.

FIG. 8 illustrates a flow channel 510 of a microfluidic device (not shown), wherein liquids introduced in three separate branches of the flow channel 510 can be combined. In the first branch 512, a sample, designated by the letter "S", is introduced. In the second branch 514, a first reagent, designated by the alphanumeric characters "R1", is introduced. In the third branch 516, a second reagent, designated by the alphanumeric characters "R2", is introduced. The flow channel 510 comprises two vents 518 and 520. The detection area 522 includes a spectrophotometer. Each vent 518 and 520 is covered by a hydrophobic membrane (not shown). The vents 518 and 520 are apertures of the type described previously.

In the AEROSET® system that is currently used for systems that do not employ microfluidics, the source of light for the spectrophotometer is typically a tungsten-halogen lamp having a wavelength ranging from about 340 nm to about 804 nm, a photometric range of from about 0.1 to about 3.0 Abs (converted to 10 mm light path length), and a light path length of 5 mm. In a microfluidic system of the type described herein, it is expected that one of ordinary skill in the art would have little difficulty in designing a near-infrared system for measuring absorbance that would provide results that are substantially equivalent to those provided by the AEROSET® system currently used. Such a system can be used for the arrangements shown in FIG. 6, FIG. 7, and FIG. 8.

Figure 9:
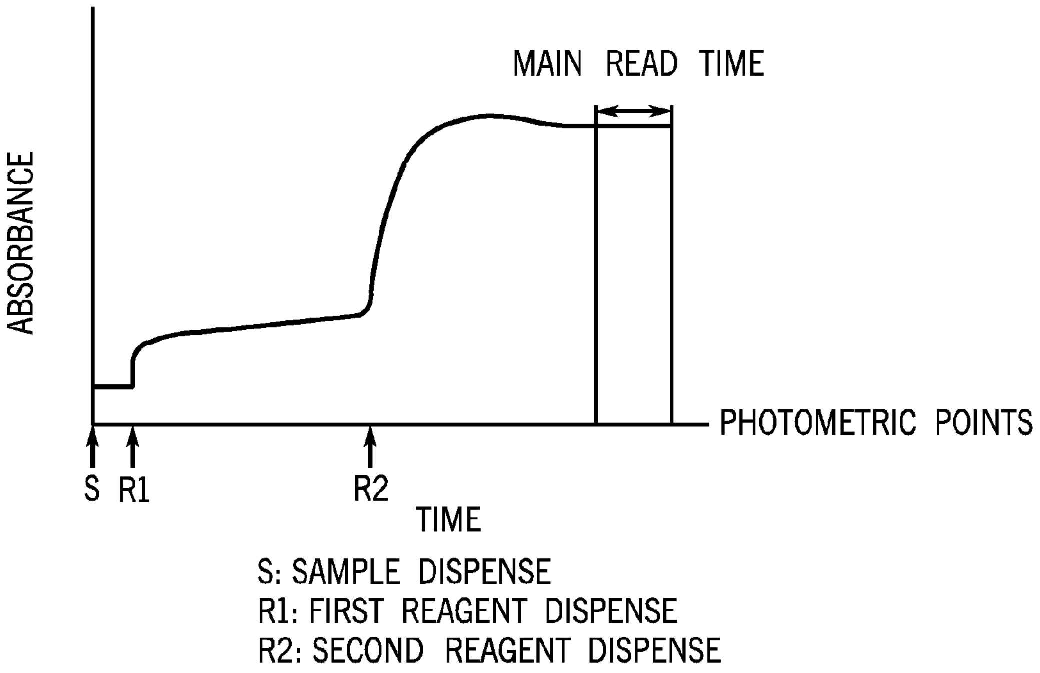
FIG. 9 is a graph illustrating absorbance as a function of time for an assay involving a sample and two reagents. The graph illustrates a curve that is characteristic of an end-point assay.
Figure 10:
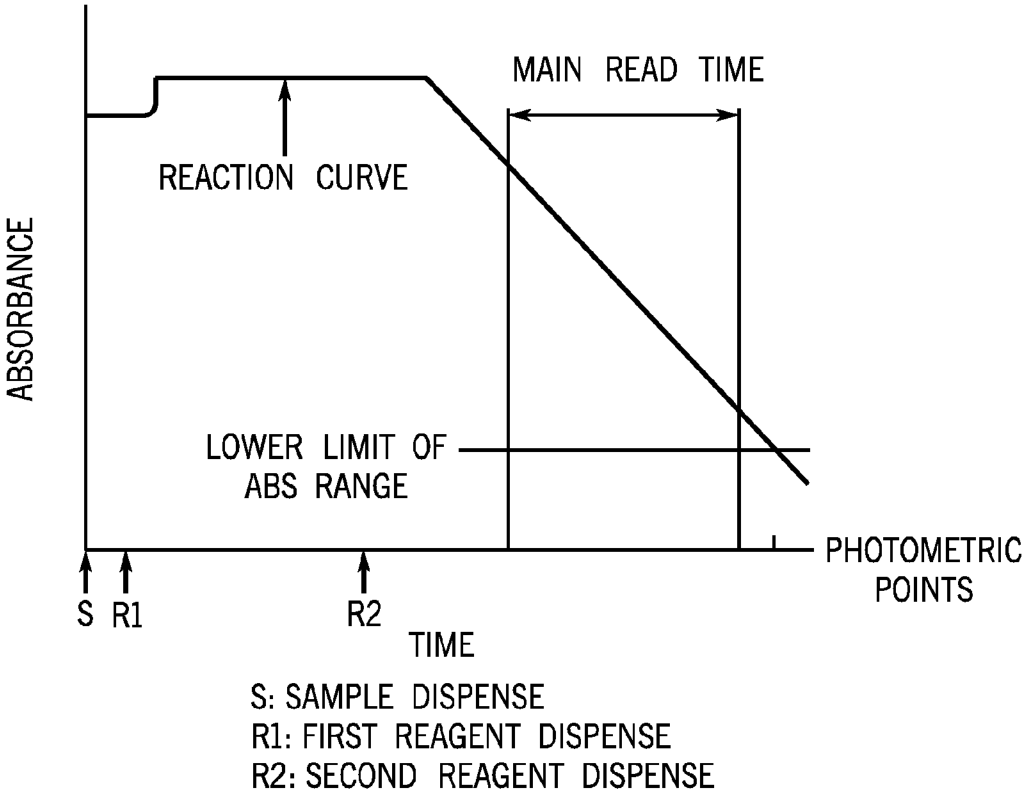
FIG. 10 is a graph illustrating absorbance as a function of time for an assay involving a sample and two reagents. The graph illustrates a curve that is characteristic of a down rate assay.

FIG. 9 is a graph illustrating absorbance as a function of time for dispensing given reagents. For end-point assays, as depicted in FIG. 9, concentration is calculated by using absorbance data obtained by an appropriate spectrophotometer. The reaction reaches equilibrium, and at that time there is little or no additional change to the absorbance readings. The absorbance readings used for calibration and to calculate results are measured during this equilibrium time. See AEROSET® Systems Operations manual, 200154-101-November 2004, pages 3-7 and 3-9 through 3-11, inclusive, all of which pages are incorporated herein. FIG. 10 is a graph illustrating absorbance as a function of time of dispensing given reagents. For rate assays, as depicted in FIG. 10, activity is calculated using the change of absorbance per minute ($\Delta$Abs/min). There is a constant change in absorbance over time. Readings are performed several times during the reaction and the absorbance change over time (activity) is calculated and used for calibration and to calculate results. Generally, at least three photometric points must be included in the reading period. The maximum number of photometric points is set by the apparatus. The rate of absorbance (change per minute) can be calculated using a linear least squares method. See AEROSET® Systems Operations manual, 200154-101-November 2004, pages 3-7 and 3-9 through 3-11, inclusive, all of which pages are incorporated herein by reference.

It is preferred that, in a branched flow channel comprising a conduit that joins with two or more branches at a junction, at least one vent be located at the position where the conduit of the given branched flow channel joins with, or intersects with, the branches of the given branched flow channel, so that gas bubbles in the flow channel can be removed efficiently. At least one hydrophobic membrane can be utilized to cover the at least one vent, whereby liquids are sealed in the flow channel(s) of the microfluidic device, while gas bubbles are allowed to pass and be removed from the flow channel(s) of the microfluidic device.

Selection of the hydrophobic membrane of the microfluidic device is based on ease of assembly. Ultrasonic welding or heat sealing are preferred for the purpose of automated assembly. Adhesives can also be used, but more assembly steps are required and the likelihood of contamination is increased on account of components from the adhesive leaching into the flow channel(s) of the microfluidic device. Ultrasonic welding is described, for example, in Ultrasonic welding—Wikipedia, the free encyclopedia, [online]. 2010 [retrieved on Oct. 21, 2010]. Retrieved from the Internet:

<URL: http://en.wikipedia.orq/wiki/Ultrasonic welding>, pages 1-6, incorporated herein by reference. An apparatus suitable for ultrasonic welding is a Branson Ultrasonic System 2000X (Branson Ultrasonics Corporation, Danbury, Conn.).

Materials that can be used to make the hydrophobic membrane include, but are not limited to, hydrophobic polypropylene, hydrophobic polyvinylidene difluoride (PVDF), hydrophobic polyethylene terephthalate, and hydrophobic polytetrafluorethylene (PTFE). The thickness of the hydrophobic membrane can range from about 60 micrometers to about 200 micrometers. The size of the pores in the hydrophobic membrane can range from about 0.1 micrometer to about 10 micrometers. A hydrophobic membrane suitable for use herein is GE Nylon, commercially available from GE Osmonics. This hydrophobic membrane can have a thickness ranging from about 65 micrometers to about 125 micrometers and a pore size ranging from about 0.1 micrometer to about 10 micrometers. See, for example, OEM GE Nylon—Hydrophobic Membranes. Datasheet [online]. General Electric Company, 2010 [retrieved on Oct., 20, 2010]. Retrieved from the Internet: <URL: http://www.osmolabstore.com/OsmoLabPaqe.dll?BuildPaqe&1&1&1021>, incorporated herein by reference. It is preferred that the hydrophobic membrane be translucent. Hydrophobic membranes suitable for use herein are commercially available from such suppliers as General Electric Company, Millipore Corporation, Billerica, Mass. 01821, and Pall Corporation, Port Washington, N.Y. 11050.

A monitoring system can be used in the process for removing gas bubbles. The monitoring system can be an optical monitoring system or an electrical monitoring system. An optical monitoring system measures the light reflected from the exterior surface of the hydrophobic membrane. An electrical monitoring system involves conductivity sensors or resistance sensors positioned at the surface of a wall at the position of the vent. An optical monitoring system is preferred for a variety of reasons. For example, light in the near infrared region of the spectrum, e.g., at a wavelength of 1950 nm, is a strong fingerprint peak for water in the near infrared region of the electromagnetic spectrum. Light in the near infrared region of the electromagnetic spectrum can penetrate to a depth of a few millimeters and illuminate the bottom wall of the hydrophobic membrane to detect the presence of gas bubbles and water. A sharp rise of absorption of light near a wavelength of 1950 nm enables the system to determine whether the gas is expelled and the information can be introduced into a microprocessor for mixing, reacting, sensing, and other operations.

The flow channel of the microfluidic device can be made by several methods, such as, for example, silica based photolithography, wet chemical etching, micro-injection molding, or micro-embossing. See, for example, U.S. Pat. No. 5,885,470, incorporated herein by reference. For additional information relating to techniques for making microfluidic devices, see, for example, Tabeling, *Introduction to Microfluidics*, Oxford University Press (2005), pages 244-281; Armani et al., Fabricating PDMS Microfluidic Channels Using a Vinyl Sign Plotter, *Lab on a Chip Technology, Volume* 1: *Fabrication and Microfluidics*, edited by Herold, K. E. and Rasooly, A., Caister Academic Press (2009), pages 9-15; Tsao et al., Bonding Techniques for Thermoplastic Microfluidics, *Lab on a Chip Technology, Volume* 1: *Fabrication and Microfluidics*, edited by Herold, K. E. and Rasooly, A., Caister Academic Press (2009), pages 45-63; Carlen et al., Silicon and Glass Micromachining, *Lab on a Chip Technology, Volume* 1: *Fabrication and Microfluidics*, edited by Herold, K. E. and Rasooly, A., Caister Academic Press (2009), pages 83-114; Cheung et al., Microfluidics-based Lithography for Fabrication of Multi-Component Biocompatible Microstructures, *Lab on a Chip Technology, Volume* 1: *Fabrication and Microfluidics*, edited by Herold, K. E. and Rasooly, A., Caister Academic Press (2009), pages 115-124; Lee, Microtechnology to Fabricate lab-on-a-Chip for Biology Applications, *Lab on a Chip Technology, Volume* 1: *Fabrication and Microfluidics*, edited by Herold, K. E. and Rasooly, A., Caister Academic Press (2009), pages 125-138; Sun et al., Laminated Object Manufacturing (LOM) Technology-Based Multi-channel Lab-on-a-Chip for Enzymatic and Chemical Analysis, *Lab on a Chip Technology, Volume* 1: *Fabrication and Microfluidics*, edited by Herold, K. E. and Rasooly, A., Caister Academic Press (2009), pages 161-172; Waddell, Laser Micromachining, *Lab on a Chip Technology, Volume* 1: *Fabrication and Microfluidics*, edited by Herold, K. E. and Rasooly, A., Caister Academic Press (2009), pages 173-184; Nguyen, Nam-Trung et al., *Fundamentals and Applications of Microfluidics*, Second Edition, ARTECH HOUSE (2006), pages 55-116, all of which references are incorporated herein by reference. The aforementioned references also indicate materials that are suitable for preparing microfluidic devices suitable for use herein.

The following non-limiting examples illustrate assays that can be carried out with the microfluidic device described herein.

EXAMPLE 1

Measurement of the concentration of cocaine enables confirmation of substance abuse. The assay for cocaine is based on the competition between a drug labeled with an enzyme and the drug from a sample of urine for a fixed number of binding sites on an antibody that specifically binds to the drug. In the absence of the drug from the sample of urine, the antibody binds to the drug labeled with the enzyme glucose-6-phosphate dehydrogenase (G6PDH), and the enzyme activity is inhibited. The G6PDH enzyme activity is determined spectrophotometrically at 340/412 nm by measuring the ability of the enzyme to convert nicotinamide adenine dinucleotide (NAD) to NADH, the reduced form of NAD.

The reactive ingredients involve two reagents, Reagent 1 and Reagent 2. Reagent 1 comprises anti-benzoylecgonine monoclonal antibodies (mouse), glucose-6-phosphate (G6P), and nicotinamide adenine dinucleotide (NAD). Reagent 2 comprises benzoylecgonine labeled with glucose-6-phosphate dehydrogenase (G6PDH).

Measurement is carried out by means of a spectrophotometer at 340/412 nm (the reading of absorbance taken at the secondary wavelength is subtracted from the reading of absorbance taken at the primary wavelength, and the difference is used as the absorbance value). Results are determined by a change in rate of absorbance, i.e., change of absorbance per minute. See, for example, AEROSET System Operations manual 200154-101-November 2004, pages 3-7 and 3-9 through 3-11, inclusive, incorporated herein by reference.

Additional information is set forth on the package insert marked ARCHITECT/AEROSET MULTIGENT Cocaine, Ref 3L40-20, incorporated herein by reference.

According to the package insert, air bubbles should be removed with a new applicator stick, if such air bubbles are present in the reagent cartridge. Alternatively, air bubbles should be allowed to dissipate by allowing the reagent to sit at the appropriate storage temperature. Reagent bubbles may interfere with proper detection of reagent level in the cartridge, causing insufficient reagent aspiration, which could adversely affect results.

EXAMPLE 2

Measurement of the concentration of creatinine enables assessment of renal function. At an alkaline pH, creatinine in the sample (serum, plasma, urine) reacts with picrate to form a creatinine picrate complex. The rate of increase in absorbance at 500 nm due to the formation of this complex is directly proportional to the concentration of creatinine in the sample.

The reactive ingredients involve two reagents, Reagent 1 and Reagent 2. Reagent 1 comprises sodium hydroxide. Reagent 2 comprises picric acid.

Measurement is carried out by means of a spectrophotometer at 500 nm. Results are determined at the stable reading after reaction.

Additional information is set forth on the package insert marked ARCH ITECT/AEROSET Creatinine, Ref 7D64-20, incorporated herein by reference. See, for example, AEROSET System Operations manual 200154-101-November 2004, pages 3-7 and 3-9 through 3-11, inclusive, incorporated herein by reference.

According to the package insert, air bubbles should be removed with a new applicator stick, if such air bubbles are present in the reagent cartridge. Alternatively, air bubbles should be allowed to dissipate by allowing the reagent to sit at the appropriate storage temperature. Reagent bubbles may interfere with proper detection of reagent level in the cartridge, causing insufficient reagent aspiration, which could adversely affect results.

EXAMPLE 3

Measurement of the concentration of ethanol enables the determination of a person's level of intoxication for legal or medical reasons. In the presence of alcohol dehydrogenase and nicotinamide adenine dinucleotide (NAD), ethanol is readily oxidized to acetaldehyde and NADH. The enzymatic reaction can be monitored spectrophotometrically at 340/412 nm.

The reactive ingredients involve two reagents, Reagent 1 and Reagent 2. Reagent 1 comprises Tris buffer. Reagent 2 comprises alcohol dehydrogenase (ADH) and NAD.

Measurement is carried out by means of a spectrophotometer at 340/412 nm (the reading of absorbance taken at the secondary wavelength is subtracted from the reading of absorbance taken at the primary wavelength, and the difference is used as the absorbance value). Results are determined at the stable reading after reaction.

Additional information is set forth on the package insert marked ARCHITECT/AEROSET MULTIGENT ETHANOL; Ref 3L36-20, incorporated herein by reference. See, for example, AEROSET System Operations manual 200154-101-November 2004, pages 3-7 and 3-9 through 3-11, inclusive, incorporated herein by reference.

According to the package insert, reagent bubbles may interfere with proper detection of reagent level in the cartridge, causing insufficient reagent aspiration, which could adversely affect results.

It should be noted that it is expected that the optical monitoring system determines the presence or absence of gas bubbles in the flow channel of the microfluidic device at a wavelength of light that is a strong fingerprint peak for water, e.g., at a wavelength of 1950 nm.

Various modifications and alterations of this invention will become apparent to those skilled in the art without departing from the scope and spirit of this invention, and it should be understood that this invention is not to be unduly limited to the illustrative embodiments set forth herein.

What is claimed is:

1. A microfluidic system comprising:

a device with a flow channel having at least one vent;

a hydrophobic membrane to cover the at least one vent, the hydrophobic membrane having a first side and a second side opposite the first side, the second side facing the vent;

a light source;

a fiber optic sensor communicatively coupled to the first side of the hydrophobic membrane, the fiber optic sensor to transmit light to the flow channel; and a light detector to detect light reflected from the first side of the hydrophobic membrane.

2. The system of claim 1, wherein the hydrophobic membrane is to vent gases.

3. The system of claim 2, wherein the hydrophobic membrane has a thickness ranging from about 60 micrometers to about 200 micrometers.

4. The system of claim 2, wherein the hydrophobic membrane has a pore size ranging from about 0.1 micrometer to about 10 micrometers.

5. The system of claim 1, wherein the light transmitted to the flow channel is in the near infrared region of the electromagnetic spectrum.

6. The system of claim 1, wherein said flow channel comprises a conduit and at least two branches converging with said conduit.

7. The system of claim 6, wherein said at least one vent is located at a junction of said conduit and said at least two branches that converge with said conduit.

8. The system of claim 1, wherein the fiber optic sensor is to transmit the light reflected by the hydrophobic membrane to the light detector.

9. The system of claim 1, wherein a cross-section of the flow channel includes at least three sides.

10. The system of claim 1, wherein a cross-section of the flow channel includes a curved side.

11. The system of claim 1, wherein the hydrophobic membrane is coupled to the flow channel via one of ultrasonic welding, heat sealing, solvent bonding or adhesive bonding.

12. The system of claim 1, wherein the flow channel has a width and a height of about 100 micrometers to about 1 millimeter.

13. The system of claim 1, wherein the hydrophobic membrane has a diameter of about 2 millimeters to about 5 millimeters.

14. The system of claim 1, wherein a first quantity of light detected by the detector when a gas bubble is adjacent the hydrophobic membrane is different than a second quantity of light detected by the detector when the gas bubble is not adjacent the hydrophobic membrane.

15. The system of claim 1, wherein the hydrophobic membrane is translucent.

16. The system of claim 1, wherein the flow channel is made by one of silica based phyotolightography, wet chemical etching, micro-injection molding or micro-embossing.

17. The system of claim 1, wherein the hydrophobic membrane comprises one of hydrophobic polypropylene, hydrophobic polyvinylidene difluoride (PVDF), hydrophobic polyethylene terephthalate or hydrophobic polytetrafluorethylene (PTFE).

18. The system of claim 1, wherein the flow channel comprises:

a first flow channel branch;

a second flow channel branch;

a third flow channel branch;

a fourth flow channel branch;

a fifth flow channel branch;

a first junction at which the first flow channel branch and the second flow channel branch converge into the third flow channel branch; and a second junction, different than the first junction, at which the third flow channel branch and the fourth flow channel branch converge into the fifth flow channel branch;

wherein the vent and the hydrophobic membrane are coupled to at least one of the first junction or the second junction.

19. The system of claim 18, wherein the first flow channel branch contains a sample.

20. The system of claim 18, wherein the fourth flow channel branch contains a sample.

21. The system of claim 18, wherein at least one of the first flow channel branch, the second flow channel branch or the fourth flow channel branch contains a reagent.

22. The system of claim 18, wherein the vent with the hydrophobic membrane is coupled to the first junction and the first flow channel branch contains a sample and the second flow channel branch contains a reagent.

23. The system of claim 18, wherein the vent with the hydrophobic membrane is coupled to the first junction and the first flow channel branch and the second flow channel branch contain reagents.

24. The system of claim 18 further comprising a spectrophotometer coupled to the fifth flow channel branch.

25. The system of claim 18 wherein the sensor is to monitor gas venting.

26. The system of claim 25, wherein the sensor uses reflectance.

27. The system of claim 25, wherein the sensor uses absorbance.

28. The system of claim 1, wherein the flow channel comprises:

a first flow channel branch;

a second flow channel branch;

a third flow channel branch;

a fourth flow channel branch; and a junction at which the first flow channel branch, the second flow channel branch and the third flow channel branch converge into the fourth flow channel; wherein the vent and the hydrophobic membrane are coupled to the junction.

29. The system of claim 28, wherein the first flow channel branch contains a sample and the third flow channel branch and the fourth flow channel branch contain reagents.

30. The system of claim 28 further comprising a spectrophotometer coupled to the fourth flow channel branch.

31. The system of claim 28 wherein the sensor is to monitor gas venting.

* * * * *